US009528923B2

(12) United States Patent
Nakata et al.

(10) Patent No.: US 9,528,923 B2
(45) Date of Patent: Dec. 27, 2016

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Hidetaka Nakata, Hachioji (JP); Tetsuya Tanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 324 days.

(21) Appl. No.: 14/190,780

(22) Filed: Feb. 26, 2014

(65) Prior Publication Data

US 2014/0175262 A1    Jun. 26, 2014

Related U.S. Application Data

(63) Continuation of application No. PCT/JP2012/066943, filed on Jul. 3, 2012.

(30) Foreign Application Priority Data

Aug. 30, 2011  (JP) ................................. 2011-187502

(51) Int. Cl.
- *G01N 15/14* (2006.01)
- *G01N 21/64* (2006.01)
- *G01N 21/76* (2006.01)

(52) U.S. Cl.
CPC .......... *G01N 15/14* (2013.01); *G01N 15/1429* (2013.01); *G01N 21/6408* (2013.01);
(Continued)

(58) Field of Classification Search
CPC ............ G01N 21/6408; G01N 21/6452; G01N 21/763; G01N 21/76; G01N 21/6458; G01N 2021/6421; G01N 2021/6419; G01N 15/1429; G01N 15/14; G01N 15/1459; G01N 15/1463; G01N 15/1456; G01N 2015/1486; G01N 33/5308; G01N 5/045; G01J 1/42

See application file for complete search history.

(56) References Cited

U.S. PATENT DOCUMENTS

| | | | |
|---|---|---|---|
| 4,251,733 A | | 2/1981 | Hirleman, Jr. |
| 5,319,575 A | * | 6/1994 | Lilienfeld ............... G01N 21/53 702/26 |

(Continued)

FOREIGN PATENT DOCUMENTS

| | | |
|---|---|---|
| EP | 1 906 172 A1 | 4/2008 |
| JP | 04-337446 A | 11/1992 |

(Continued)

OTHER PUBLICATIONS

Extended European Search Report dated Oct. 20, 2014, issued in related EP Application No. 12770835.2 (10 pages).

(Continued)

*Primary Examiner* — John Lee
(74) *Attorney, Agent, or Firm* — Westerman, Hattori, Daniels & Adrian, LLP

(57) ABSTRACT

There is provided optical analysis techniques in the scanning molecule counting method using the light measurement with a confocal or multiphoton microscope in which the measuring unit time in the light measurement is set to an appropriate value in order to surely detect an approximately bell shape profile of the signal of a light-emitting particle and avoid excessive increase data volume of time series light intensity data. The inventive optical analysis technique of detecting light of a light-emitting particle in a sample solution generates time series light intensity data of light from a light detection region detected during moving the (Continued)

position of the light detection region of a microscope in the sample solution and detects in the data a signal indicating light from each light-emitting particle individually. The measuring unit time is determined based on the size and the moving speed of the light detection region.

27 Claims, 6 Drawing Sheets

(52) U.S. Cl.
CPC ..... *G01N 21/6452* (2013.01); *G01N 21/6458* (2013.01); *G01N 21/76* (2013.01); *G01N 21/763* (2013.01); *G01N 2021/6419* (2013.01); *G01N 2021/6421* (2013.01)

(56) References Cited

U.S. PATENT DOCUMENTS

| | | | |
|---|---|---|---|
| 5,866,336 A | 2/1999 | Nazarenko et al. | |
| 6,280,960 B1 | 8/2001 | Carr | |
| 6,376,843 B1* | 4/2002 | Palo | G01J 3/4406 250/458.1 |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,710,871 B1 | 3/2004 | Goix | |
| 6,782,297 B2 | 8/2004 | Tabor | |
| 6,856,391 B2 | 2/2005 | Garab et al. | |
| 6,927,401 B1 | 8/2005 | Palo | |
| 7,914,734 B2* | 3/2011 | Livingston | B01L 3/5085 250/428 |
| 8,269,965 B2* | 9/2012 | Kask | G01N 15/02 250/458.1 |
| 8,284,484 B2 | 10/2012 | Hoult et al. | |
| 9,068,944 B2* | 6/2015 | Tanabe | G01N 21/6408 |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0013086 A1* | 1/2003 | Kask | G01N 15/02 435/6.12 |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2005/0260660 A1 | 11/2005 | van Dongen et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2007/0020645 A1* | 1/2007 | Kask | G01N 15/02 435/6.12 |
| 2008/0052009 A1 | 2/2008 | Chiu et al. | |
| 2009/0142765 A1* | 6/2009 | Vacca | G01N 1/38 435/6.12 |
| 2009/0159812 A1 | 6/2009 | Livingston | |
| 2010/0033718 A1 | 2/2010 | Tanaami | |
| 2010/0177190 A1 | 7/2010 | Chiang et al. | |
| 2010/0202043 A1 | 8/2010 | Ujike | |
| 2010/0230612 A1* | 9/2010 | Kask | G01N 15/02 250/459.1 |
| 2013/0230874 A1* | 9/2013 | Hanashi | G01N 21/6452 435/15 |
| 2014/0175262 A1* | 6/2014 | Nakata | G01N 21/6408 250/206 |

FOREIGN PATENT DOCUMENTS

| | | |
|---|---|---|
| JP | 10-512952 A | 12/1998 |
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-017127 A | 1/2010 |
| JP | 2010-190730 A | 9/2010 |
| JP | 2011-002415 A | 1/2011 |
| JP | 2011-508219 A | 3/2011 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008-080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/032955 A1 | 3/2012 |
| WO | 2012/032981 A1 | 3/2012 |
| WO | 2012/039352 A1 | 3/2012 |

OTHER PUBLICATIONS

Extended European Search Report dated Mar. 18, 2015, issued in corresponding European Application No. 12828331.4.(7 pages).
Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report dated Mar. 29, 2011, issued in related PCT/JP2011/053482.
International Preliminary Report on Patentability (PCT/IPEA/409) issued in related PCT/JP2011/053482, (dated Mar. 30, 2012).
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481, (dated Jun. 15, 2012).
Goodwin, Peter et al., "Rapid Sizing of Individual Fluorescently Stained DNA Fragments by Flow Cytometry," Nucleic Acids Research, 1993, vol. 21, No. 4, p. 803-806.

(56) References Cited

OTHER PUBLICATIONS

Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
International Search Report dated Nov. 29, 2011, issued in related PCT/JP2011/071196.
Guo, Xiang-Qun et al., "Use of a Long-Lifetime Re(I) Complex in Fluorescence Polarization Immunoassays of HighMolecular-Weight Analytes", Analytical Chemistry, Feb. 1998, vol. 7, No. 3, p. 632-637.
International Search Report dated Jun. 26, 2012, issued in related PCT/JP2012/057731.
International Search Report dated Jun. 26, 2012, issued in related PCT/JP2012/058840.
International Search Report dated Mar. 5, 2013, issued in related PCT/JP2013/052446.
Supplementary European Search Report dated Feb. 13, 2014, issued in related EP application No. 11826797.0.
International Search Report dated Nov. 29, 2011, issued in related PCT/JP2011/072939.
Final Office Action dated Sep. 28, 2015, issued in U.S. Appl. No. 13/746,968 (24 pages).
Final Office Action dated Sep. 29, 2015, issued in U.S. Appl. No. 13/946,091 (23 pages).
Office Action dated May 14, 2015, issued in counterpart Chinese Patent Application No. 201280042499.1, w/English translation (34 pages).
International Search Report, dated Aug. 14, 2012, issued in corresponding application No. PCT/JP2012/066943.
Kinjo, Masataka, "Single molecule protein, nucleic acid, and enzyme assays and their procedures: Single molecule detection by fluorescence correlation spectroscppy", Protein, Nucleic acid Enzyme, Japan 1999, vol. 44, No. 9, pp. 1431-1438.
Mayer-Alms, F., J., "Nanoparticle Immunoassays: A new Method for Use in Molecular Diagnostics and High Throughput Pharmaceutical Screening based on Fluorescence Correlation Spectroscopy", R. Rigler, edit, Springer, Berlin Germany, 2000, pp. 204-224.
Kato, Noriko, et al., "Gene Medicine", Japan, 2002, vol. 6, No. 2, pp. 271-277.
Kask, Peet, et al., "Fuorescence-intensity distribution analysis and its application in biomolecular detection technology", PNAS,Nov. 23, 1999, vol. 96, No. 24, pp. 13756-13761.

* cited by examiner

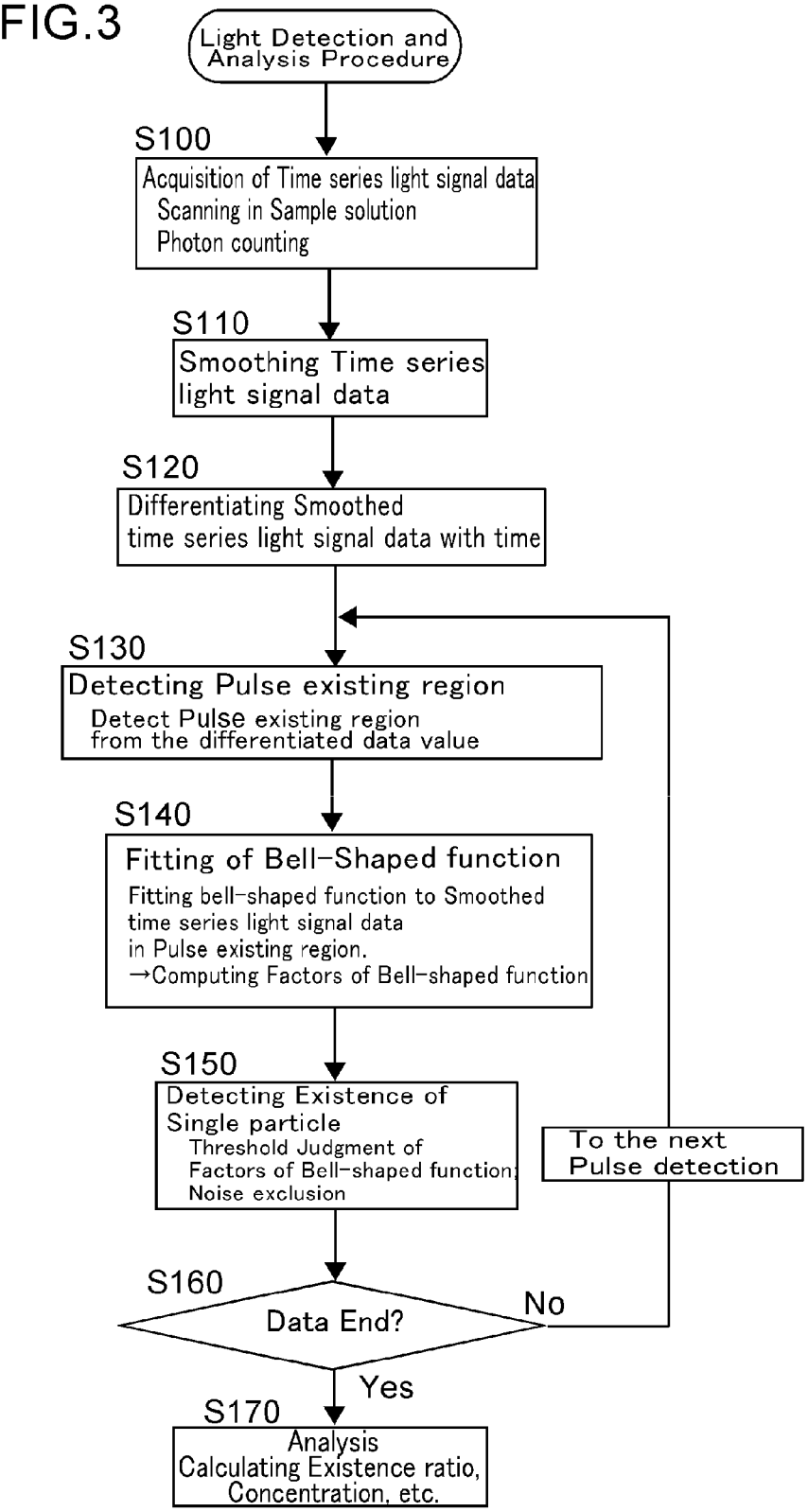

FIG.5
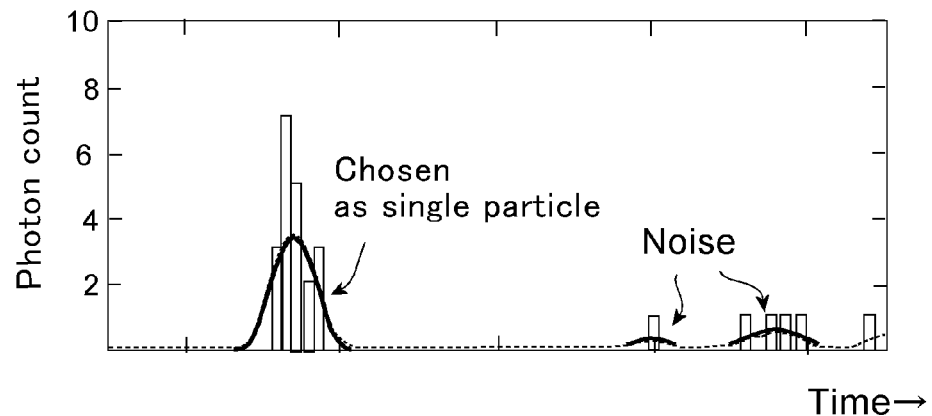
FIG.6A BIN TIME=20μs
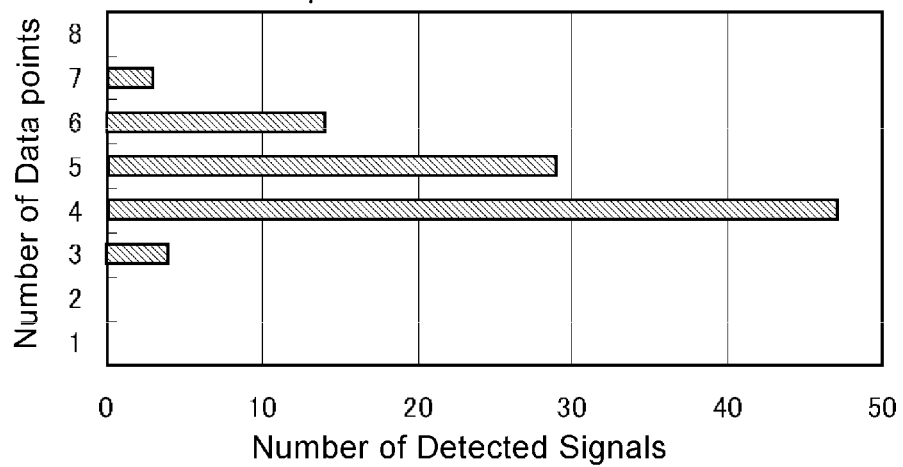
FIG.6B BIN TIME=30μs
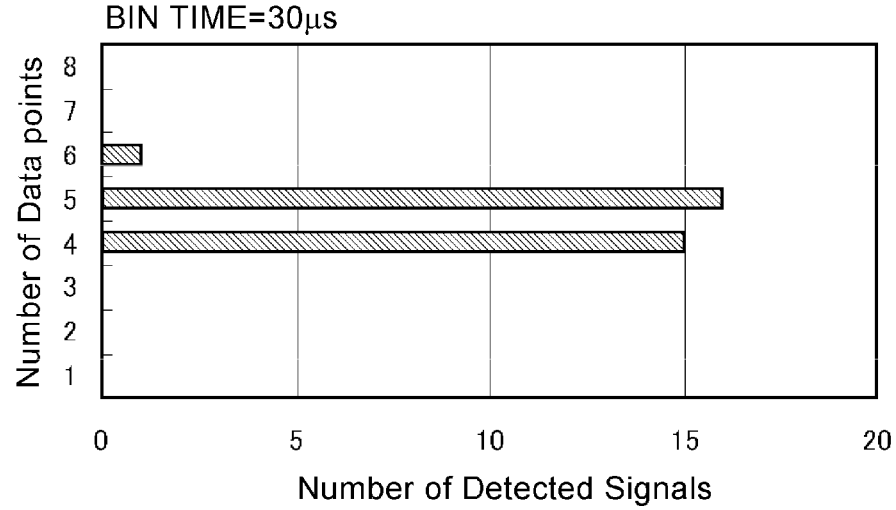

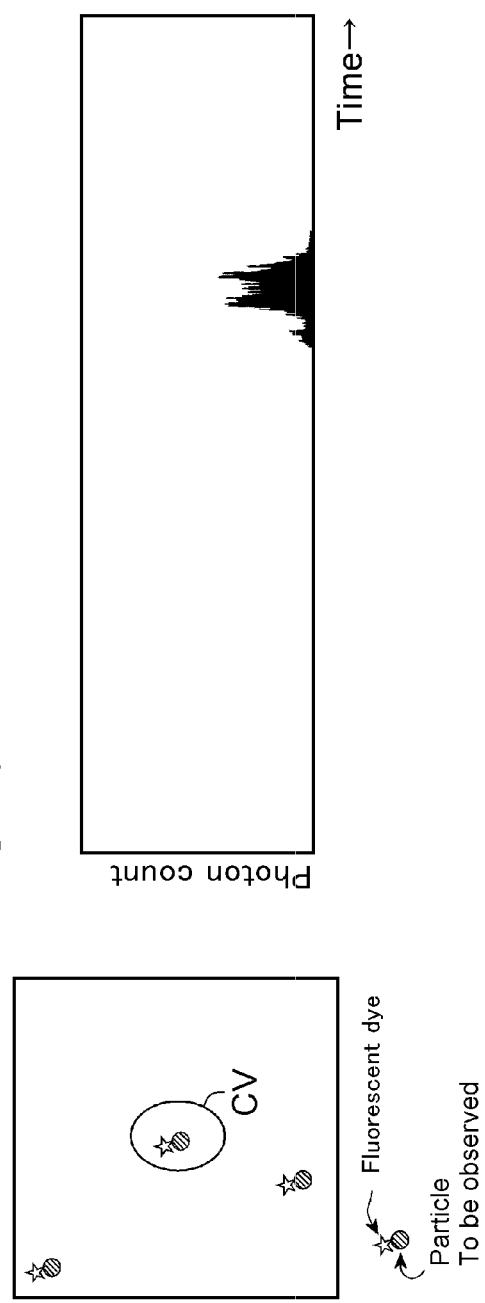
FIG.7A High Concentration (e.g. ~ 1nM)
FIG.7B Low Concentration (e.g. ~ 1pM)

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kinjo; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In the above-mentioned scanning molecule counting method, more concretely, light intensity values (or photon count values) measured sequentially during the moving of the position of a light detection region in a sample solution are recorded as time series light intensity data, and in that data, an increase of the light intensity value indicating light emitted from a light-emitting particle (a signal indicating light of a light-emitting particle) is detected. In this respect, generally, in an optical analysis device performing the scanning molecule counting method, a light intensity, emitted from a single light-emitting particle and reaching to a photodetector, varies with the position of the light-emitting particle in the light detection region, and typically, the light intensity becomes its maximum when the position of the light-emitting particle is in the almost central region of the light detection region (in the followings, the position from which the light intensity of a light-emitting particle in the light detection region becomes its maximum is called the "maximum intensity point".), while the light intensity gradually reduces as the position of the light-emitting particle is closer to the circumference of the light detection region. Namely, the intensity distribution of detected light emitted from a light-emitting particle in a light detection region (In the followings, simply referred to as "light intensity distribution in the light detection region") has an approximately bell shaped profile in which the intensity reduces from the maximum intensity point toward the circumference. Thus, when a light-emitting particle passes through a light detection region in an approximately straight line, the profile of the increase of the light intensity value indicating the light emitted from the light-emitting particle on time series light intensity data becomes an approximately bell shaped profile corresponding to the light intensity distribution in the light detection region, and accordingly, the increase of the light intensity value indicating the light emitted from a light-emitting particle, i.e., the signal of the light-emitting particle will be detectable by judging whether or not the profile of a certain increase of the light intensity value is an approximately bell shaped profile assumed in a light-emitting particle passing through the inside of the light detection region.

On the other hand, the profile of a signal of a light-emitting particle appearing on time series light intensity data is influenced by the time resolution of the time series light intensity data in its generation. Typically, in an optical analysis device performing the scanning molecule counting method, the light intensity is measured with the light amount, received with a photodetector, per predetermined measuring unit time. For instance, when the light measurement is conducted by the photon counting, usually, the light intensity is expressed with the number of photons which have reached to and been detected with the photodetector in every measuring unit time (bin time) arbitrarily set in the order from sub-microseconds to milliseconds. Thus, when the light intensity value is sequentially measured with the light amount per this measuring unit time and the time series light intensity data is generated, it becomes possible to acquire the approximately bell shaped profile of the light intensity value increase with higher precision as the measuring unit time is shorter, i.e., as the time resolution is higher, while the approximately bell shaped profile could not be obtained if the measuring unit time is too long, i.e., if the time resolution is too low. That is, it is preferable that the measuring unit time is shorter in order to detect the signal of a light-emitting particle with high precision; however, as the measuring unit time is shorter, the data volume of time series light intensity data will increase so that the cost will increase, also. Moreover, the profile of a signal of a light-emitting particle obtained in time series light intensity data is also dependent upon the moving speed of a light detection region. Namely, as the moving speed of a light detection region is higher, the time in which a light-emitting particle is encompassed in the light detection region becomes shorter so that the time of the appearance of the signal of the single light-emitting particle will become shorter.

Thus, the main object of the present invention is to provide a way of setting the measuring unit time in the light measurement in the scanning molecule counting method to an appropriate value in order to surely detect an approximately bell shaped profile of a signal of a light-emitting particle and avoid excessive increase of the data volume of time series light intensity data.

Solution to Problem

According to one aspect of the present invention, the above-mentioned object is achieved by an optical analysis device which detects light from a light-emitting particle dispersed and moving at random in a sample solution using an optical system of a confocal microscope or a multiphoton microscope, comprising: a light detection region mover which moves a position of a light detection region of the optical system of the microscope in the sample solution; a light detector which detects a light amount coming from the light detection region in every measuring unit time; and a signal processor which generates time series light intensity data of the light from the light detection region detected with the light detector in every measuring unit time during moving the position of the light detection region in the sample solution and detects a signal indicating light from each light-emitting particle individually in the time series light intensity data; wherein the measuring unit time is determined based on a size and a moving speed of the position of the light detection region.

In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, typically, the light detector detects the light from the light detection region by the photon counting in which (a) photon(s) arriving in every predetermined measuring unit time (bin time) is/are counted, and in that case, the time series light intensity data becomes time series photon count data. In this connection, in this specification, "a signal of a light-emitting particle" means a signal expressing light from a light-emitting particle, unless noted otherwise.

As understood from the above, in the basic structure of the present invention, i.e., the scanning molecule counting method, the light detection is sequentially performed while the position of the light detection region is moved in a sample solution, namely, while the inside of the sample solution is scanned with the light detection region. Then, it is expected that, when the light detection region moving in the sample solution encompasses a randomly moving light-emitting particle, the light from the light-emitting particle is detected by the light detector and thereby the existence of one particle will be detected. Thus, in the sequentially detected light, a signal indicating light from a light-emitting particle is individually detected, and thereby, the existences of individual particles are detected one by one, and accordingly, diverse information on the conditions of the particles in the solution will be acquired. In this structure, as already noted, in detecting light, the light detector detects the light amount coming from the light detection region in every measuring unit time while the magnitude of the light amount or the light intensity detected per measuring unit time is changed into electric signals, is sent to the signal processor, and constitutes time series light intensity data. In that case, if the measuring unit time is too long, the characteristic profile of the signal of a light-emitting particle will be lost, while, if the measuring unit time is too short, the data volume will become huge. In this regard, whether or not the characteristics of the profile of the signal of a light-emitting particle is lost in time series light intensity data is determined by the relation between the length of the signal of the light-emitting particle appearing on the time series light intensity data and the length of the measuring unit time, and the length of the signal of the light-emitting particle is dependent upon the size and the moving speed of the position of the light detection region. Then, in the present invention, the length of the measuring unit time is set based on the size and the moving speed of the position of the light detection region so that the characteristic profile of the signal of a light-emitting particle can be caught and the data volume can be suppressed.

Regarding the setting of the above-mentioned measuring unit time, more in detail, the length of the measuring unit time should be set relatively shorter than the length of the signal of a light-emitting particle on time series light intensity data in order to capture the characteristic profile of the signal of the light-emitting particle. The length of the signal of a light-emitting particle becomes longer as the size of the light detection region is larger, and it becomes shorter as the moving speed is higher, and consequently, the measuring unit time may be set longer as the size of the light detection region is larger, and it may be set shorter as the moving speed is higher. Further, the length of the signal of a light-emitting particle is equal to the passage duration of one light-emitting particle passing through the light detection region, so that the passage duration will be given by [the size of the light detection region]/[the moving speed of the light detection region]. (Here, [the size of the light detection region] is the size or diameter of the light detection region in the direction parallel to the moving direction of the light detection region].) Thus, the measuring unit time may be set longer as the passage duration of the light-emitting particle is longer.

Moreover, with respect to the setting of the measuring unit time, yet more in detail, in order to catch the characteristic profile of the signal of a light-emitting particle on time series light intensity data therefrom, at least two datum points in the time direction are required (If the number of the datum point is one, although only the presence or absence of a signal can be found, the information on the profile of the signal will be completely extinguished.). Accordingly, preferably, the measuring unit time is set to be less than a half of the passage duration in one light-emitting particle passing through the light detection region. In this respect, for the passage duration of a light-emitting particle, an approximate theoretical value may be used. As noted above, the passage duration of a light-emitting particle is given by [the size of the light detection region]/[the moving speed of the light detection region]. Here, as described in detail later, the moving speed of the light detection region is determined with the velocity of the changing of the direction of a mirror in the optical system or the moving of a sample container, and its value can be comparatively accurately estimated. However, although the size of a light detection region can be estimated, using the wavelength of light and the numerical aperture of an objective, as the outer diameter of a spherical or elliptical surface on which the intensity of the excitation light becomes $1/e^2$ of the intensity at the center in the light detection region, it is difficult to precisely define the surface region on which the excitation light intensity becomes substantially 0. Then, using, as an approximate value of [the size of the light detection region], the maximum size or the maximum diameter (the approximate diameter of the light detection region) of the spherical or elliptical surface on which the excitation light intensity becomes $1/e^2$ of the intensity at the center in the direction parallel to the direction of movement of the light detection region, the value given with [the approximate diameter of the light detection region]/[the moving speed of the light detection region] (the approximate passage duration) may be employed as the passage duration of a light-emitting particle.

Furthermore, according to the results of experiments in the embodiment shown later, it has been shown that, when at least three datum points, more preferably, four or more datum points are included during one light-emitting particle passing through a light detection region, a signal of a light-emitting particle can be more accurately detected on time series light intensity data. Here, one datum point is given in one measuring unit time. Thus, in the above-mentioned device, preferably, the measuring unit time may be set so that a passage duration of one light-emitting particle passing through the light detection region will overlap with at least three measuring unit times. In this regard, the passage duration of one light-emitting particle may be the above-mentioned approximate passage duration or a time value acquired experimentally beforehand (usually, the approximate passage duration is shorter than the passage duration acquired experimentally.).

In the processes of the signal processor of the above-mentioned inventive device, the judgment of whether or not one light-emitting particle enters into the light detection region from a signal in the successively detected values from the light detector may be performed based on the profile of the time series signal indicating light detected in the light detector as already noted. In this regard, in an embodiment, typically, it may be designed that the entry of one light-emitting particle into a light detection region is detected when a signal with a larger intensity than a predetermined threshold value is detected. More concretely, as explained in the following column of embodiments, usually, the profile of a signal indicating light from a light-emitting particle exhibits a bell-shaped pulse form having an intensity beyond a certain degree in the time series detected values, i.e., light intensity data, of the light detector, while the profile of a noise does not form a bell-shaped pulse, or its intensity is small. Then, the signal processor of the inventive device may be designed to detect on time series light intensity data a pulse form signal which has an intensity exceeding a predetermined threshold value as a signal indicating light from a single light-emitting particle. The "predetermined threshold value" can be experimentally set to an appropriate value.

Furthermore, the object to be detected in the inventive device is the light from a single light-emitting particle, and thus, light intensity is extremely weak, and when one light-emitting particle is a single fluorescent molecule or several molecules, the light is stochastically emitted from the light-emitting particle, so that minute time gaps can be generated in the signal values. If such a gap is generated, the identification of a signal corresponding to the existence of one light-emitting particle will become difficult. Then, the signal processor may be designed to apply smoothing treatment to time series light intensity data so that minute time gaps in signal values can be ignored, and to detect as a signal indicating light from a single light-emitting particle a bell-shaped pulse form signal having an intensity beyond a predetermined threshold value in the smoothed time series light intensity data.

The moving speed of the position of the light detection region in a sample solution in the above-mentioned inventive device may be changeable appropriately based on the characteristics, number density or concentration of a light-emitting particle in the sample solution. The manner of the light detected from a light-emitting particle may vary with the characteristics, number densities or concentration of a light-emitting particle in a sample solution. Especially, when the moving speed of the light detection region becomes quick, the light amount obtained from one light-emitting particle will be reduced, and thus, in order to measure the light from one light-emitting particle accurately or with sufficient sensitivity, it is preferable that the moving speed of the light detection region can be changed appropriately.

Moreover, the moving speed of the position of the light detection region in the sample solution is preferably set to be higher than the diffusional moving velocity of a light-emitting particle to be an object to be detected (the average moving speed of a particle owing to the Brownian motion). As explained above, the inventive device detects a light-emitting particle individually by detecting the light emitted from a light-emitting particle when the light detection region passes through the existence position of the light-emitting particle. However, when the light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of a light-emitting particle, and thereby it becomes possible to make one light-emitting particle associated with one signal. In this regard, since the diffusional moving velocities differ depending upon light-emitting particles, it is preferable that the moving speed of the light detection region can be changed appropriately according to the characteristics (especially, the diffusion constant) of the light-emitting particle as described above.

The moving of the position of the light detection region in a sample solution may be achieved by an arbitrary way. For example, the position of the light detection region may be changed by changing the optical path of the optical system of the microscope using a galvanometer mirror adopted in a laser scan type light microscope, or the position of the sample solution may be moved (e.g. by moving the stage of a microscope) so that the position of the light detection region will be moved in the sample solution. The movement track of the position of the light detection region may be set arbitrarily, for example, may be selected from circular, elliptical, rectangular, straight linear and curvilinear ones. Especially, in the case of changing the position of the light detection region by changing the optical path of the optical system of the microscope, the moving of the light detection region is quick, and since neither mechanical vibration nor hydrodynamic action occurs substantially in the sample solution, it is advantageous in that a measurement can be conducted under a stable condition without a light-emitting particle to be an object to be detected being influenced by a dynamic action.

In one of manners of the above-mentioned present invention, the number of light-emitting particles encompassed in the light detection region may be counted by counting the number of the selectively detected signals (The counting of particles). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

The processes of the optical analysis technique of conducting a light detection with moving the position of a light detection region in a sample solution and detecting the signal from each light-emitting particle individually in the above-mentioned inventive device, in which the measuring unit time of the light detection is set in consideration of the size and the moving speed of the position of the light detection region, can be realized with a general-purpose computer. Thus, according to another aspect of the present invention, there is provided a computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising: moving a position of a light detection region of the optical system of the microscope in the sample solution; detecting a light amount coming from the light detection region in every measuring unit time determined based on a size and a moving speed of the position of the light detection region during moving the position of the light detection region in the sample solution to generate time series light intensity data; and detecting individually a signal indicating light from each light-emitting particle using the time series light intensity data. In this regard, typically, in the step of detecting light from the light detection region to generate time series light intensity data, the light from the light detection region is detected by the photon counting in which the number of photons arriving every measuring unit time (bin time) is counted, and in that case, the time series light intensity data is time series photon count data. In the present application, "computer readable storage device" does not cover transitory propagating signal per se. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this structure, more in detail, the measuring unit time may be set longer as the size of the light detection region is larger, shorter as the moving speed is higher, or longer as the passage duration of a light-emitting particle is longer. Further, preferably, the measuring unit time is less than a half of the approximate passage duration in one light-emitting particle passing through the light detection region, and more preferably, the measuring unit time may be set so that the passage duration in one light-emitting particle passing through the light detection region will overlap with at least three measuring unit times.

Further, also in the above-mentioned computer program, the individual detection of a signal indicating light from each light-emitting particle may be performed based on the profile of the time series signal. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Furthermore, the moving speed of the position of the light detection region in the sample solution may be appropriately changed based on the characteristics, the number density or concentration of the light-emitting particle in the sample solution, and preferably, the moving speed of the position of the light detection region in the sample solution is set higher than the diffusion moving velocity of the light-emitting particle to be the object to be detected. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in this computer program, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

According to the above-mentioned inventive device or computer program, there is realized a novel optical analysis method of conducting detection of the light of each light-emitting particle with moving the position of a light detection region in a sample solution, in which the measuring unit time of the light detection is set in consideration of the size and the moving speed of the position of the light detection region. Thus, according to the present invention, there is further provided an optical analysis method of detecting light from a light-emitting particle dispersed and moving at random in a sample solution using an optical system of a confocal microscope or a multiphoton microscope, comprising steps of: moving a position of a light detection region of an optical system of the microscope in the sample solution; detecting a light amount coming from the light detection region in every measuring unit time together with moving the position of the light detection region in the sample solution and generating time series light intensity data; and detecting individually a signal indicating light from each light-emitting particle in the time series light intensity data, wherein a measuring unit time is determined based on the size and the moving speed of a position of the light detection region.

Even in this method, typically, in the step of detecting light from the light detection region to generate time series light intensity data, the light from the light detection region is detected by the photon counting in which the number of photons arriving every measuring unit time (bin time) is counted, and in that case, the time series light intensity data is time series photon count data. And more in detail, the measuring unit time may be set longer as the size of the light detection region is larger, shorter as the moving speed is higher, or longer as the passage duration of a light-emitting particle is longer. Further, preferably, the measuring unit time is less than a half of the approximate passage duration in one light-emitting particle passing through the light detection region, and more preferably, the measuring unit time may be set so that the passage duration in one light-emitting particle passing through the light detection region will overlap with at least three measuring unit times.

Further, also in the above-mentioned method, the individual detection of a signal indicating light from each light-emitting particle may be performed based on the profile of the time series signal. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle.

Furthermore, the moving speed of the position of the light detection region in the sample solution may be appropriately changed based on the characteristics, the number density or concentration of the light-emitting particle in the sample solution, and preferably, the moving speed of the position of the light detection region in the sample solution is set higher than the diffusion moving velocity of the light-emitting particle to be the object to be detected. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in the above-mentioned method, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Thus, according to the present invention, in order that the characteristic profile of the signal of a light-emitting particle on light intensity data can be caught while data volume can be controlled, the measuring unit time in the light detection is set based on the size and the moving speed of the position of a light detection region. According to this structure, in the detection of the signal of a light-emitting particle, it is avoided to make the time resolution in data vainly high and cause increasing data volume, so that the cost can be saved. Further, also in trying the saving of data volume, the setting of the measuring unit time can be performed with grasping the limit where the characteristics of the profile of the signal of a light-emitting particle can be caught more certainly, and accordingly, it becomes possible to maintain the accuracy in separation of the signals of light-emitting particles and noises. Furthermore, since the saving of data volume can be achieved while the accuracy in separation of the signals of the light-emitting particle and a noise is maintained, the burdens in the signal processing in the detection of the signal of the light-emitting particle is reduced.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the scanning molecule counting method according to the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism which moves the horizontal position of a micro plate to move the position of the light detection region in a sample solution.

FIGS. 2A and 2B are a schematic diagram explaining the principle of the light detection and a schematic diagram of the variation of the measured light intensity with time in the scanning molecule counting method to which the present invention is applied, respectively. FIG. 2C is a drawing explaining about the relations between intensity changes of light from a light-emitting particle and measuring unit times. FIG. 2D is a schematic drawing of a light detection region, showing schematically that the passage duration of a light-emitting particle changes with passing positions.

FIG. 3 are diagrams showing the procedures of the scanning molecule counting method performed in accordance with the present invention in the form of a flow chart.

FIGS. 4A and 4B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining an example of the signal processing step of the detected signals in the procedure for detecting the existence of a light-emitting particle from the measured time series light intensity data (change in time of photon count) in accordance with the scanning molecule counting method.

FIG. 5 shows examples of measured photon count data (bar graph): curves obtained by carrying out the smoothing of the data (dotted line); and Gauss functions fitted on the pulse existing region (solid line). In the drawing, the signals attached with "noise" are disregarded as signals due to noises or contaminants.

FIGS. 6A and 6B show a distribution of the numbers of datum points included in the pulse signals detected as a light-emitting particle signal. FIG. 6A indicates the case that the BINTIME was set to 20 μseconds, and FIG. 6B indicates the case that the BINTIME was set to 30 μseconds.

Figure 1A:
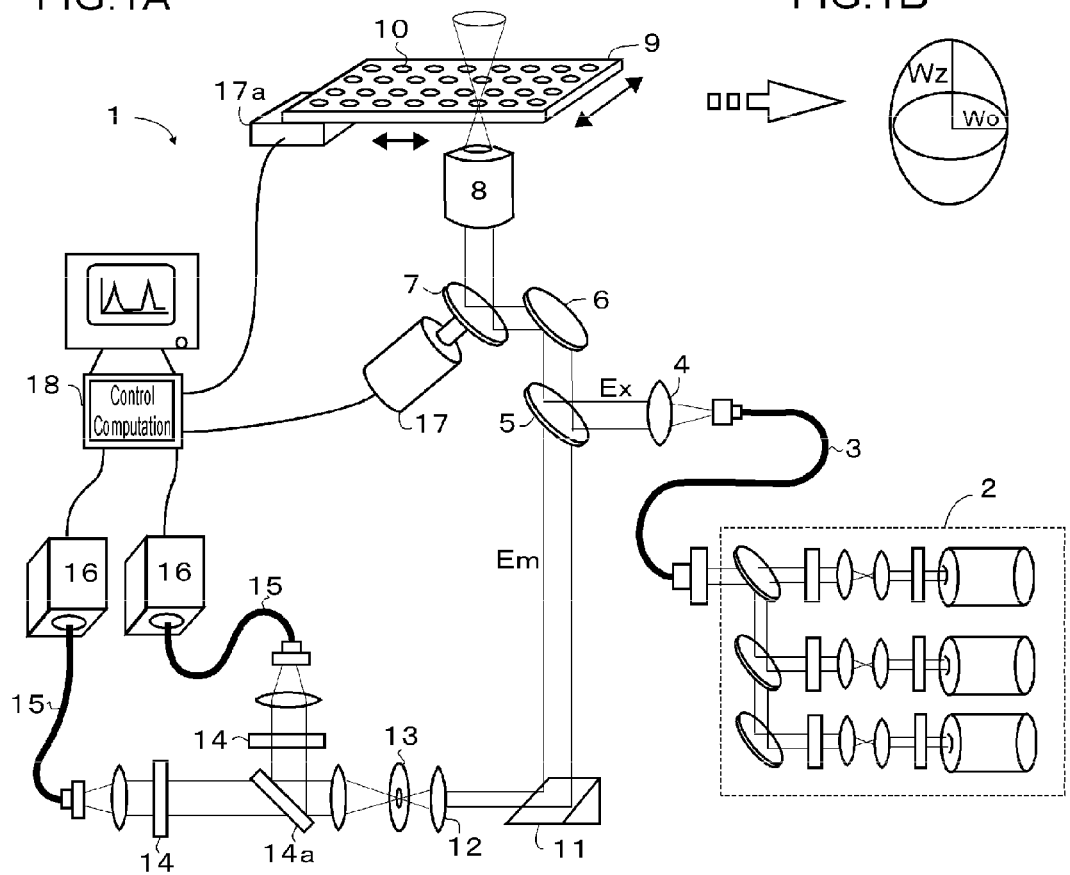

FIGS. 7A and 7B show examples of the time variation of the photon count (light intensity) obtained in a conventional optical analysis technique computing fluorescence intensity fluctuation, where FIG. 7A shows a case that the particle concentration is at a level providing a sufficient precision in the measurement, and FIG. 7B shows a case that the particle concentration in a sample is significantly lower than the case of FIG. 7A.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a- - - Dichroic mirror or Polarization beam splitter
15 - - - Multi-mode optical fiber
16 - - - Photodetector
17 - - - Mirror deflector
17a- - - Stage position changing apparatus
18 - - - Computer

DESCRIPTION OF EMBODIMENTS

In the followings, preferable embodiments of the present invention are described in detail.

Structure of Optical Analysis Device

Figure 1B:
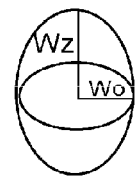

In the basic structure, an optical analysis device which realizes the optical analysis technique according to the present invention is a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent particles or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL, in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the center light intensity.), which focal region is called as "confocal volume". Furthermore, in the present invention, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurement can be achieved even when there are two or more specimens.

Figure 1C:
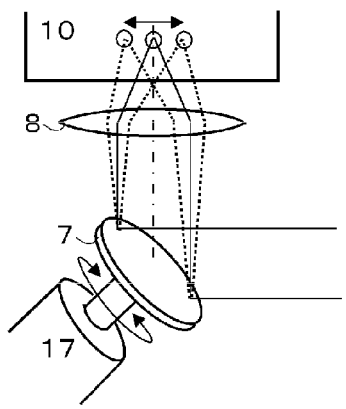
Figure 1D:
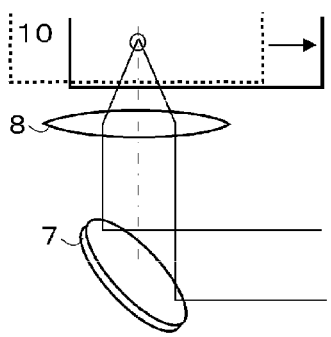

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of moving the absolute position of a light detection region). This mirror deflector 17 may be the same as that of a galvanomirror device equipped on a usual laser scan type microscope. Or, alternatively, as illustrated in FIG. 1D, the stage position changing apparatus 17a may be operated in order to move the horizontal position of the container 10 (micro plate 9), into which the sample solution has been dispensed, to move the relative position of the light detection region in the sample solution (the type of moving the absolute position of a sample solution). In either of the ways, in order to attain a desired moving pattern of the position of the light detection region, the mirror deflector 17 or the stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.) In this regard, although not illustrated, the position of the light detection region may be moved in the vertical direction by moving the objective 8 or stage up and down.

In the case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may be provided, and thereby, it may be designed that, when two or more kinds of light-emitting particles having different emission wavelengths are included in the sample, the light therefrom can be detected separately in accordance with the wavelengths. Moreover, with respect to the light detection, it may be designed to use light, polarized in a predetermined direction, as excitation light and select, as the detected lights, components in the direction vertical to the polarization direction of the excitation light. In that case, a polarizer (not shown) is inserted in an excitation light optical path, and a polarization beam splitter 14a is inserted in a detected light optical path. According to this structure, it becomes possible to reduce the background light in the detected light substantially. The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

The Principle of the Inventive Method

As described in the column of "Summary of Invention", briefly, in the inventive optical analysis technique, the measuring unit time (bin time of photon counting) of the light detection process in the scanning molecule counting method is set in order that the characteristics of the profile of the approximately bell shape of the signal of a light-emitting particle does not disappear on time series light intensity data so that the signal of the light-emitting particle can be detected precisely without making the data volume excessive. In the following, the principle of the scanning molecule counting method and the setting of the measuring unit time in the present invention are explained.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques, such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 7A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 7B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring time should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

Figure 2A:
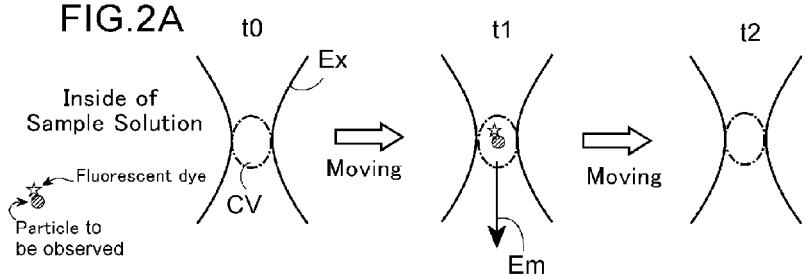
Figure 2B:
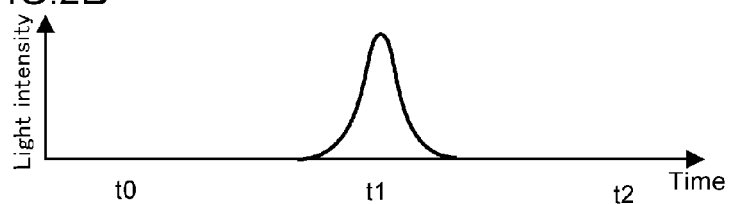

As the processes to be performed in the scanning molecule counting method, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path or by moving the horizontal position of the container 10 (micro plate 9) into which the sample solution is dispensed, as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Principle of the Setting of Measuring Unit Time

In the light intensity data acquired with time progress by the above-mentioned scanning molecule counting method with the photodetector 16 (time series light intensity data), there are contained noises due to heat noises of the photodetector, background light, etc. other than pulse form signals owing to the lights from light-emitting particles. Then, in detecting a signal of a light-emitting particle from the time series light intensity data, typically, the shape characteristic of a pulse form signal found in the time series light intensity data, for instance, the peak intensity, width, the degree of the approximation to the shape of a bell shaped function, such as Gauss function, (the correlation coefficient of the Gauss function fitting) are referred to. And, a pulse signal having the shape characteristic in the range assumed in the pulse signal of a light-emitting particle is judged as a signal of a light-emitting particle, and the other pulse signals are judged as noise signals.

By the way, in the light measurement sequentially performed in the scanning molecule counting method as described above, the light intensity value is the light amount received with the photodetector per predetermined measuring unit time. In the case of the light measurement based on the photon counting, the light intensity is expressed by the number of photons which have reached to and been detected with the photodetector in every measuring unit time (bin time), arbitrarily set in the order of sub-μsecond to msecond. Thus, actually, the time series light intensity data consists of the datum points indicating the respective light amounts or photon counts in the corresponding measuring unit times aligned in time series, and thus, the profile of the signal of the light-emitting particle which appears there will change in accordance with the length of the measuring unit time or bin time. That is, as the length of the measuring unit time or bin time becomes longer, the shape characteristic of the pulse signal owing to a light-emitting particle will disappear in much more extent, and consequently, it will becomes difficult to precisely discriminate between the signal of a light-emitting particle and a noise signal. Thus, the precise discrimination between the signal of a light-emitting particle and a noise signal can be achieved by setting the length of the measuring unit time or bin time enough shorter than the length of the signal of a light-emitting particle so that the shape characteristic of the signal of the light-emitting particle can be caught. However, as the length of the measuring unit time or bin time becomes shorter, the number of datum points increases and the data volume becomes huge, causing the increase of data processing load or cost.

Figure 2C:
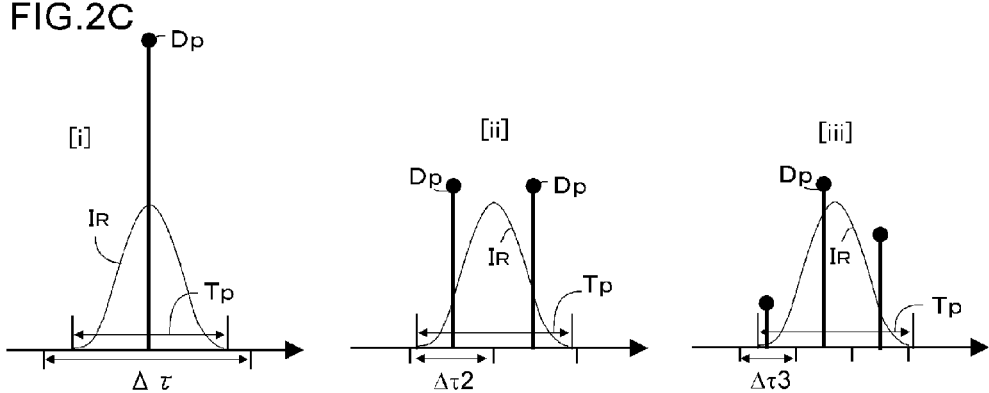

Then, in the present invention, the length of the measuring unit time or bin time in light measurement is set so that the signal of a light-emitting particle and a noise signal can be discriminated from one another in accordance with the shape characteristic of the signal of the light-emitting particle without increasing data points unnecessarily. FIG. 2C shows relations between the profiles $I_R$ and lengths Tp of pulse signals of a light-emitting particle and the measuring unit times Δτ. Referring to the drawings, first, when the measuring unit time is longer than the length Tp of the pulse signal of a light-emitting particle, namely, in the case of:

$$Tp < \Delta\tau 1, \quad [i]$$

for the profile $I_R$ of the pulse signal of a light-emitting particle, only one datum point Dp is assigned. In this case, the characteristics of the approximately bell shaped profile of the pulse signal of a light-emitting particle disappears while its remaining information is only the magnitude of the intensity value, and therefore, it is very difficult to detect the pulse signal of a light-emitting particle based on the shape characteristic of the pulse signal of the light-emitting particle. Further, when the measuring unit time satisfies:

$$Tp > \Delta\tau 2 \geq \tfrac{1}{2}Tp, \quad [ii]$$

two datum points Dp are assigned to the profile $I_R$ of the pulse signal of a light-emitting particle, however, also in this case, the approximately bell shaped characteristic, namely, the value variation in the order of small, large and small in the time direction has disappeared in the values of the datum points Dp, and thus, it is difficult to detect a pulse signal of a light-emitting particle based on the shape characteristic of the pulse signal of the light-emitting particle. On the other hand, when the measuring unit time is shorter than one half of the length Tp of the pulse signal of a light-emitting particle, namely, in the cases of:

$$\tfrac{1}{2}Tp > \Delta\tau 3 \geq \tfrac{1}{3}Tp, \quad [\text{iii}]$$

$$\tfrac{1}{3}Tp > \Delta\tau 4 \geq \tfrac{1}{4}Tp, \quad [\text{iv}]$$

$$\tfrac{1}{4}Tp > \Delta\tau 5 \geq \tfrac{1}{5}Tp, \quad [\text{v}]$$

similarly in the followings, at least three datum points Dp are present, and thus, the approximately bell shaped characteristic of the value variation in the order of small, large and small along the time direction is preserved, and accordingly, it becomes possible to detect the pulse signal of a light-emitting particle based on the shape characteristic of the pulse signal of the light-emitting particle.

Actually, according to the experimental results in Embodiment 1 described later, in the pulse signals detected as a signal of a light-emitting particle, at least three datum points Dp were included within the generation period of each signal. Thus, from the above-mentioned considerations and the experimental results of Embodiment 1, the length of the measuring unit time should be set so that three or more datum points Dp can be encompassed in the generation period of the pulse signal of a light-emitting particle. Here, the generation period of the pulse signal of a light-emitting particle corresponds to the duration in which the light-emitting particle has been passing through the inside of the light detection region. And, one datum point corresponds to one measuring unit time. Therefore, the length of the measuring unit time should just be set so that the passage duration in one light-emitting particle passing through a light detection region will overlap with at least three measuring unit times. In this connection, it should be understood that, in this condition, the passage duration of a light-emitting particle may not be more than the sum of three measuring unit times. What is important in the above-mentioned condition is that three or more datum points exist in the passage duration of a light-emitting particle, and therefore, as long as this condition is satisfied, the sum of three measuring unit times may exceed the passage duration of the light-emitting particle, and such a case belongs to the scope of the present invention, also. Furthermore, according to the experimental results in Embodiment 1 described later, the pulse signal of a light-emitting particle can be detected more accurately, when four or more datum points Dp are encompassed in the generation period. Accordingly, the length of a measuring unit time may be set so that four or more datum points Dp may be encompassed in the passage duration in one light-emitting particle passing through a light detection region. (Namely, the length of a measuring unit time may be set so that the passage duration in one light-emitting particle passing through a light detection region may overlap with at least four measuring unit times.).

The concrete setting of a measuring unit time or a bin time may be conducted based on the size of a light detection region and the moving speed of the light detection region. As described in the column of "Summary of Invention", the length of the signal of the light-emitting particle, i.e., the passage duration in one light-emitting particle passing through a light detection region, to be the basis of a suitable measuring unit time or bin time is theoretically given by:

[Size of a light detection region]/[Moving speed of a light detection region] (1), and thus, the measuring unit time or bin time may be appropriately determined with reference to this theoretical value. As understood from the above-mentioned expression (1), the passage duration of a light-emitting particle becomes longer as the size of a light detection region is larger, and becomes shorter as the moving speed of the light detection region is higher, and accordingly, while following this, the measuring unit time or bin time may be increased or decreased.

Figure 2D:
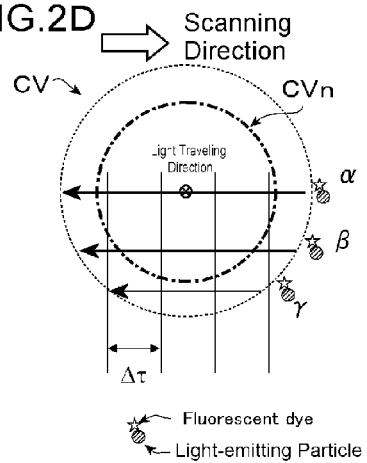

In this connection, with respect to the above-mentioned expression (1), the moving speed of a light detection region can be uniquely computed precisely from the track and the cycle time of the light detection region, but, the size of the light detection region is the length of the track of a light-emitting particle in the light detection region, namely, the length of the light detection region in the direction parallel to its moving direction (scanning direction), and thus, it changes depending upon the passing position of a light-emitting particle in the light detection region. As shown in FIG. 2D, a light detection region is a sphere or an ellipsoid, and thus, [The size of a light detection region] in the expression (1), corresponding to the distance across a sphere or an ellipsoid, differs in accordance with the position in the direction vertical to the scanning direction of the light detection region. For example, in FIG. 2D, the passage length of light-emitting particles become shorter in the order of α, β, γ. Moreover, it is also difficult to strictly define the boundary of a light detection region. Namely, although a light detection region is defined by the condensing condition of excitation light (and the diameter of a pinhole), it is not easy to theoretically precisely determine the boundary on which the excitation light intensity (or detected light intensity) becomes substantially 0. Then, as the boundary of a light detection region, the spherical or elliptical surface CVn on which the light intensity becomes $1/e^2$ of the center intensity in the light detection region may be employed. And the diameter 2Wo of the spherical or elliptical surface on which the light intensity becomes $1/e^2$ of the center intensity in the light detection region is given approximately by $$2Wo = 1.22 \cdot \lambda / (D/2f) \quad (2).$$

(where λ is the excitation wave length; D is the diameter of the incident light beam; and f is the focal distance of the objective.). So, the measuring unit time or bin time may be determined through referring to the value, computed from the expression (1) as an approximate value of the passage duration in one light-emitting particle passing through the light detection region (namely, the length Tp of the pulse signal of the light-emitting particle) with employing the value computed with the expression (2) as an approximate value (approximate passage duration) of the size of a light detection region. In the determining of the measuring unit time or bin time from the approximate passage duration, as already noted, the passage duration in one light-emitting particle passing through a light detection region should encompass at least three datum points, and thus, the measuring unit time or bin time may be set, for example, to be less than half, and preferably ⅓ of the approximate passage duration. Alternatively, the measuring unit time or bin time may be determined so that it will encompass at least three datum points in the approximate passage duration. Further, by considering that the passage duration becomes shorter as the passing position of a light-emitting particle is closer to the circumference of a light detection region, with reference to the approximate passage duration, the measuring unit time or bin time may be set to be a time enough shorter than ⅓ of the approximate passage duration, e.g. about its ⅙, so that at least three datum points will be encompassed in the passage duration of a light-emitting particle passing through the circumference of the light detection region, in order to detect more certainly the signal of a light-emitting particle passing through the circumference of the light detection region. Of course, the passage duration in one light-emitting particle passing through a light detection region can be determined beforehand through an experiment, and therefore, the measuring unit time or bin time may be determined so that at least three datum points, obtained experimentally, may be encompassed in the passage duration of a light-emitting particle.

Operation Processes of Scanning Molecule Counting Method

In the embodiment of the scanning molecule counting method in accordance with the present invention with the optical analysis device 1 as illustrated in FIG. 1A, concretely, there are conducted (1) a preparation of a sample solution containing light-emitting particles; (2) a process of measuring the light intensity of the sample solution and (3) a process of analyzing measured light intensities. FIG. 3 shows the processes in this embodiment in form of the flow chart.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is a particle which emits no light, there is used a particle to which a light emitting label (a fluorescence molecule, a phosphorescence molecule, and a chemiluminescent or bioluminescent molecule) is attached in an arbitrary manner. Typically, the sample solution is an aqueous solution, but not limited to this, and it may be an organic solvent or other arbitrary liquids.

(2) Measurement of Light Intensity of a Sample Solution (FIG. 3—Step 100)

The measurement of the light intensity in the optical analysis by the scanning molecule counting method of the present embodiment may be conducted in a manner similar to a measurement process of light intensity in FCS or FIDA except that the mirror deflector 17 or the stage position changing apparatus 17a is driven to move the position of the light detection region within the sample solution (scanning the sample solution) during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or the stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into electric signals and transmits them to the computer 18, which generates the time series light intensity data from the transmitted signals and stores them in an arbitrary manner. In this regard, the photodetector 16 is typically a super high sensitive photodetector which can detect an arrival of a single photon, and thus when the detection of light is performed by the photon counting, the time series light intensity data may be time series photon count data. The bin time in the photon counting is set appropriately so that at least three datum points will be encompassed in an approximate passage duration or the passage duration of a particle obtained experimentally, as noted above.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

Figure 4A:
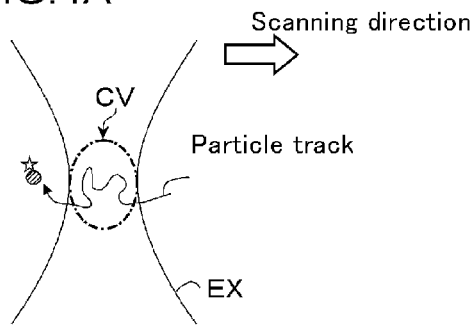

By the way, with respect to the moving speed of the position of the light detection region, in order to perform quantitatively precisely individual detection of a light-emitting particle to be observed from the measured time series light intensity data or the counting of the number of light-emitting particles, it is preferable to set the moving speed to a value quicker than the moving speed in the random motion, i.e., the Brownian motion of a light-emitting particle, while satisfying the condition of the above-mentioned Expression (1). Since the particle to be observed in the inventive optical analysis technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity changes at random (As noted, the excitation light intensity in the light detection region is reduced from the peak at the center of the region toward its outside.), so that it would become difficult to determine a significant light intensity change corresponding to each light-emitting particle. Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each light-emitting particle becomes almost uniform in the time series light intensity data as illustrated in the most upper row of FIG. 4C (When a light-emitting particle passes through the light detection region in an approximately straight line, the profile of the light intensity change is similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius Wo (confocal volume) by the Brownian motion is given from the equation of the relation of mean-square displacement:

$$(2Wo)^2 = 6D \cdot \Delta t \quad (3)$$

as:

$$\Delta t = (2Wo)^2/6D \quad (4),$$

and thus, the velocity of the light-emitting particle moving by the Brownian motion (diffusional moving velocity) Vdif, becomes approximately $$V\text{dif} = 2Wo/\Delta t = 3D/Wo \quad (5)$$

Then, with reference to this, the moving speed of the position of the light detection region may be set to a value sufficiently quicker than Vdif. For example, when the diffusion coefficient of a particle to be observed is expected to be about $D=2.0\times10^{-10}$ µm²/s, Vdif will be $1.0\times10^{-3}$ m/s, supposing Wo is about 0.62 µm, and therefore, the moving speed of the position of the light detection region may be set to its 10 times or more, 15 mm/s, etc. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(3) Analysis of Light Intensity

When the time series light intensity data is obtained by the above-mentioned processes, there are performed the detection of a signal of a light-emitting particle, the counting of light-emitting particles, and various analyses, such as concentration calculation, etc. in the computer 18 through processes in accordance with programs memorized in a storage device.

(i) Individual Detection of a Signal of a Light-Emitting Particle (Steps 110-160)

Figure 4B:
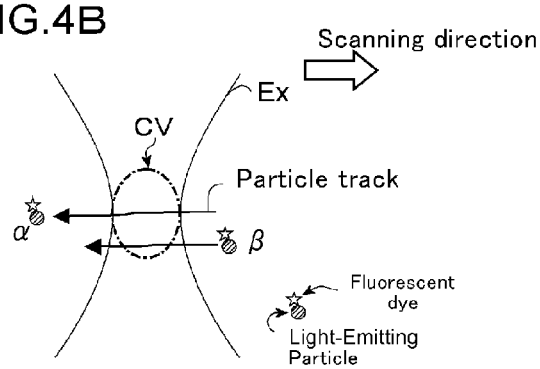

When the time series light intensity data has been generated, the process of detecting (a) signal(s) of (a) light-emitting particle(s) individually on the light intensity data. As already noted, when the track of one light-emitting particle in its passing through the light detection region is approximately straight as shown in FIG. 4B, the light intensity variation in the signal corresponding to the particle in the time series light intensity data has a bell shaped profile reflecting the light intensity distribution in the light detection region determined by the optical system. Thus, basically in the scanning molecule counting method, when the time width $\Delta \tau$ for which the light intensity value exceeding an appropriately set threshold value Ith continues on the light intensity data is in a predetermined range, the signal having the profile of the light intensity may be judged to correspond to one particle having passed through the light detection region, and thereby one light-emitting particle is detected. And a signal whose light intensity has not exceed beyond the threshold value Ith or whose time width $\Delta \tau$ is not within the predetermined range is judged as noise or a signal of a contaminant. Further, when the light intensity distribution in the light detection region can be assumed as a Gaussian distribution:

$$I = A \cdot \exp(-2t^2/a^2) \quad (6),$$

and when the intensity A and the width a, computed by fitting Expression (6) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

Figure 4C:
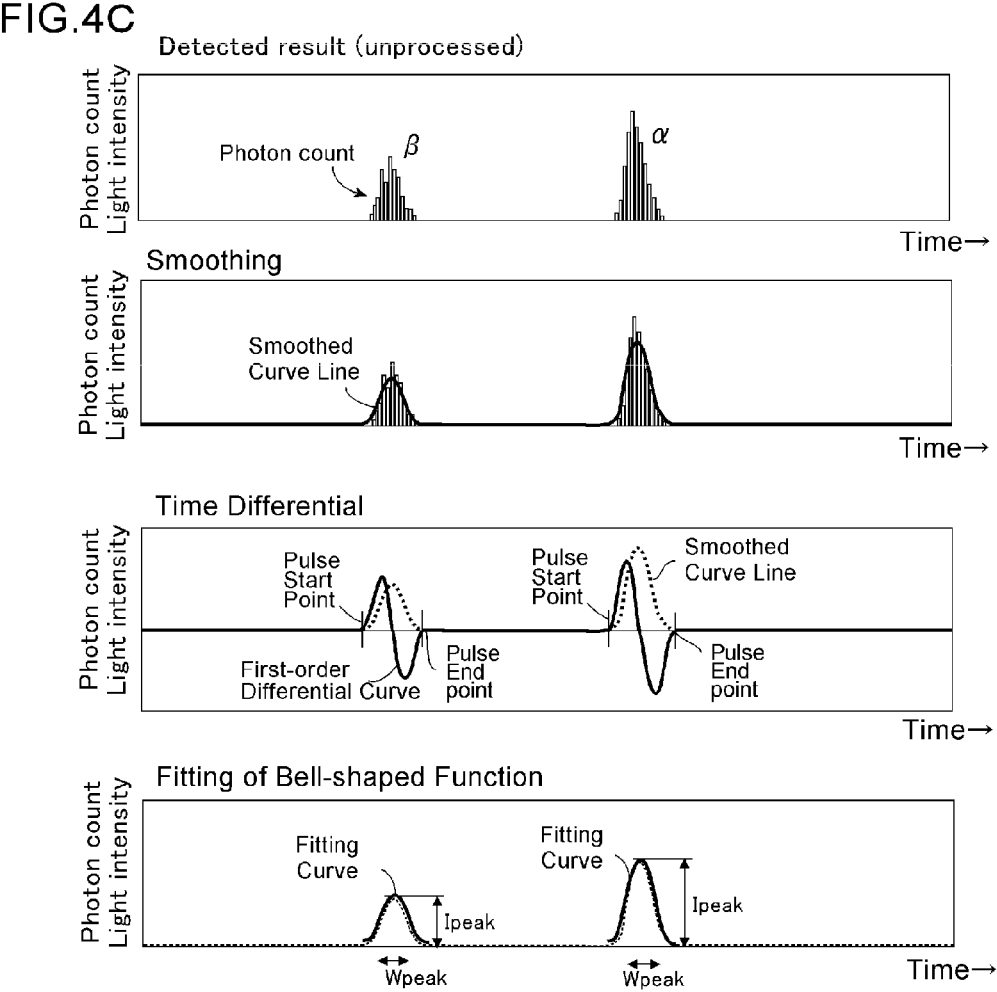

As one example of the processes of detection of (a) signal(s) on the light intensity data, first, a smoothing treatment is performed to the light intensity data (FIG. 4C, the most upper row "detected result (unprocessed)") (FIG. 3—step 110, FIG. 4C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the light intensity data after the smoothing treatment, in order to detect a time domain (pulse existing region) in which a significant pulse form signal (referred to as "pulse signal" hereafter) exists, the first differentiation value with time of the smoothed light intensity data is computed (step 120). As illustrated in FIG. 4C, the mid-low row "time differential", in the time differential value of light intensity data, the value variation increases at the time of the signal value change, and thereby, the start point and the end point of a significant signal can be determined advantageously by referring to the time differential value.

After that, significant pulse signals are detected sequentially on the light intensity data (Steps 130-160). Concretely, first, on the time-differential value data of the light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed light intensity data in the pulse existing region (FIG. 4C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (5), it may be Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges, etc. (Step 150). Accordingly, the signal, whose computed parameters of the bell-shaped function are judged to be within the ranges assumed in a light signal corresponding to one light-emitting particle, as shown in FIG. 5 left, is judged as a signal corresponding to one light-emitting particle, and thereby one light-emitting particle has been detected. On the other hand, a pulse signal, whose computed parameters of the bell-shaped function are not within the assumed ranges, as shown in FIG. 5 right, is disregarded as noise. In this regard, together with the detection of signals of light-emitting particles, the counting of the number of signals, i.e., the counting of light-emitting particles, may be conducted.

The searching and judging of a pulse signal in the above-mentioned processes of steps 130-150 may be repetitively carried out throughout light intensity data (step 160). In this connection, the processes for detecting individually a signal from the light intensity data may be performed by an arbitrary way, other than the above-mentioned procedures.

(iii) Determination of Light-Emitting Particle Concentration

In the case that the number of light-emitting particles is determined by counting the number of signals of detected light-emitting particles, if the volume of the whole region through which the light detection region has passed is computed out by an arbitrary way, the number density or concentration of the light-emitting particle in the sample solution can be determined from the number of light-emitting particles and the volume (Step 170).

The volume of the whole region through which the light detection region has passed may be theoretically computed out with the wavelength of excitation light or detected light, the numerical aperture of lenses and the adjustment condition of the optical system, but the volume may be determined experimentally, for instance, using the number of light-emitting particles detected by performing, with a solution having a known light-emitting particle concentration (a reference solution), the light intensity measurement, detection of (a) light-emitting particle(s) and their counting under the same condition as the measurement of a sample solution to be tested, and the light-emitting particle concentration of the reference solution. Concretely, for example, supposing the number of detected light-emitting particles is N in a reference solution of the light-emitting particle concentration C, the whole volume Vt of the region through which the light detection region has passed is given by:

$$Vt = N/C \quad (7).$$

Alternatively, by preparing the plurality of solutions of different light-emitting particle concentrations and performing the measurement for each of the solutions, the average value of the computed Vts may be employed as the whole volume Vt of the region though which the light detection region has passed. Then, when Vt is given, the concentration c of the light-emitting particle of the sample solution, whose counting result of the light-emitting particles is n, is given by:

$$c = n/Vt \quad (8)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (7)) between concentrations C and light-emitting particle numbers N of various standard light-emitting particles for assumed moving patterns of the light detection region, so that a user of the device can appropriately use the memorized information on the relation in conducting an optical analysis.

In order to verify the validity of the present invention explained above, the experiments described below were conducted. In this regard, it should be understood that the following embodiments illustrate the validity of the present invention only, not intended to limit the scope of the present invention.

Embodiment 1

In the scanning molecule counting method, the influence of the measuring unit time to detection of light-emitting particle signals was verified by changing variously the measuring unit time in the light detection process.

For a sample solution, a solution containing, as a light-emitting particle, a fluorescent dye ATTO0633 (ATTO-TEC) in a phosphate buffer (including 0.1% Pluronic F-127) at 10 pM was prepared. In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned sample solution in accordance with the manner explained in the above-mentioned "(2) Measurement of Light Intensity of a Sample Solution". In that time, a 633-nm laser light was used for excitation light, and, using a band pass filter, the light of the wavelength bands, 660 to 710 nm, was measured, generating time series photon count data. The laser power of excitation light was set to 200 µW. The moving speed of the position of the light detection region in the sample solution was set to 15 mm/sec.; BIN TIME, 1 µsec., and the measurement was performed for 1 second.

In the data processing after the light measurement, first, for the acquired time series photon count data, the reconstruction of the time series photon count data was performed so that BIN TIME became 10, 20, 30, 50 or 100 µseconds, respectively (For example, in the reconstruction data of BIN TIME of 10 µseconds, one point was generated by summing the photon counts of ten points in the datum points of 1 µsecond of BIN TIME.). Subsequently, in each of the reconstructed time series photon count data, individual detection of signals of light-emitting particles and the counting of the number of the signals were performed. In the detection of signals of light-emitting particles, in accordance with the way described in "(i) Individual detection of a signal of a light-emitting particle" and steps 110-160 in FIG. 3, a smoothing treatment was applied to the time series photon count data, and after determining the start points and end points of pulse signals in the smoothed data, a Gauss function was fit to each pulse signal by the least-squares method, and the peak intensity, pulse width (full width at half maximum), and correlation coefficient (in the Gauss function) were determined. And only a pulse signal satisfying the following conditions was extracted as a signal corresponding to a light-emitting particle:

20 µseconds<pulse width<400 µseconds

Peak intensity>1 [pc/10 µsec.]

Correlation coefficient>0.90, (A)

Table 1 shows the numbers of signals, detected as a light-emitting particle signal in each of the reconstructed time series photon count data and the data volumes of reconstruction data.

TABLE 1

| BIN TIME (μsec.) | The Number of Detected Signals | Data Volume (KB) |
| --- | --- | --- |
| 10 | 97 | 489 |
| 20 | 106 | 245 |
| 30 | 32 | 163 |
| 50 | 0 | 98 |
| 100 | 0 | 49 |

With reference to the above-mentioned results, in the cases that BIN TIME was 10 μseconds-20 μseconds, there were no large changes in the number of detected signals, while the number of the detected signals reduced greatly in the case that BIN TIME was 30 μseconds and no signals were detected in the cases that BIN TIME became 50 μseconds microseconds or more. Since the diameter of the light detection region was adjusted to about 1 μm and the moving speed of the light detection region was 15 mm/second, the approximate passage duration in which a light-emitting particle passed through the light detection region was about 67 μsec. The above-mentioned results suggest that the characteristics of the profile of the approximately bell shape of a light-emitting particle signal is maintained so that the detection of a light-emitting particle can be performed accurately, when BIN TIME is set preferably to be less than half of an approximate passage duration and more preferably to be about its ⅓. Furthermore, without making BIN TIME short more than needed, it also becomes possible to suppress the data volume.

Moreover, the number of the datum points encompassed in each signal detected as a signal of a light-emitting particle was checked in the case that BIN TIME was 20 μsec. and the case that BIN TIME was 30 μsec. FIG. 6A shows the numbers of detected pulse signals to the numbers of the datum points encompassed in the respective detected pulse signals in that the case that BIN TIME was 20 μsec. and FIG. 6B shows the numbers of detected pulse signals to the numbers of the datum points encompassed in the respective detected pulse signals in the case that BIN TIME was 30 sec. As understood with reference to the drawings, at least three datum points were encompassed in the signal detected as a signal of a light-emitting particle. Further, especially, there were many detected number of the pulse signals encompassing four or five datum points. This is considered to be because the characteristic of the bell shaped profile of a light-emitting particle signal has been maintained better when four or more datum points were encompassed in a detected pulse signal. Also, comparing FIG. 6A and (B) with one another, the reason that the number of detected pulse signals in the case that BIN TIME is 30 μsec. reduced as compared with the case that BIN TIME was 20 μsec. is considered to be because BIN TIME became long when BIN TIME was 30 μsec. so that the datum points encompassed in the signal of each light-emitting particle reduced, and thereby the characteristic of the bell shaped profile of the signal of the light-emitting particle which passed the position near the circumference of a light detection region so that its passage duration became short disappeared.

Thus, as understood from the results of the above-mentioned embodiments, by setting the measuring unit time in the scanning molecule counting method according to the teaching of the present invention, it becomes possible to detect the signal of a light-emitting particle with sufficient accuracy based on the approximately bell shaped profile and avoid excessive increase of the data volume of time series light intensity data.

The invention claimed is:

1. An optical analysis device which detects light from a light-emitting particle dispersed and moving at random in a sample solution using an optical system of a confocal microscope or a multiphoton microscope, comprising:
    a light detection region mover which moves a position of a light detection region of the optical system in the sample solution;
    a light detector which detects a light amount coming from the light detection region in every measuring unit of time; and
    a signal processor which generates time series light intensity data of the light from the light detection region detected with the light detector in every measuring unit of time during moving the position of the light detection region in the sample solution and detects a signal indicating light from each light-emitting particle individually in the time series light intensity data by detecting a time variation of light intensity having a profile expected in a light from one light-emitting particle moving relatively in the light detection region as a signal of one light-emitting particle;
    wherein the measuring unit of time is based on a size and a moving speed of a position of the light detection region such that the measuring unit of time is less than a half of an approximate passage duration of one light-emitting particle passing through the light detection region.

2. The device of claim 1, wherein the measuring unit of time is set to be longer as a size of the light detection region is larger and to be shorter as the moving speed of the light detection region is higher.

3. The device of claim 1, wherein the measuring unit of time is set so that a passage duration of one light-emitting particle passing through the light detection region overlaps with at least three measuring units of time.

4. The device of claim 1, wherein the signal processor counts a number of signals indicating light from the light-emitting particles detected individually to count a number of the light-emitting particles detected during moving the position of the light detection region.

5. The device of claim 1, wherein the light detection region mover moves the position of the light detection region at velocity quicker than a diffusion moving velocity of the light-emitting particle.

6. The device of claim 1, wherein the light detection region mover changes an optical path of the optical system to move the position of the light detection region of the optical system in the sample solution.

7. The device of claim 1, wherein the signal processor detects that one light-emitting particle has entered into the light detection region when a signal indicating light having a larger intensity than a predetermined threshold value is detected.

8. The device of claim 1, wherein the signal processor smoothes the time series light intensity data, and detects a bell-shaped pulse form signal having an intensity beyond the predetermined threshold value in the smoothed time series light intensity data as a signal indicating light from the single light-emitting particle.

9. The device of claim 1, wherein the signal processor determines a number density or concentration of the light-emitting particle in the sample solution based on a number of the detected light-emitting particles.

10. An optical analysis method of detecting light from a light-emitting particle dispersed and moving at random in a sample solution using an optical system of a confocal microscope or a multiphoton microscope, comprising:
   (a) moving a position of a light detection region of an optical system in the sample solution;
   (b) detecting a light amount coming from the light detection region in every measuring unit of time together with moving the position of the light detection region in the sample solution and generating time series light intensity data; and
   (c) detecting individually a signal indicating light from each light-emitting particle in the time series light intensity data by detecting a time variation of light intensity having a profile expected in a light from one light-emitting particle moving relatively in the light detection region as a signal of one light-emitting particle,
   wherein a measuring unit of time is based on the size and the moving speed of a position of the light detection region such that the measuring unit of time is less than a half of an approximate passage duration of one light-emitting particle passing through the light detection region.

11. The method of claim 10, wherein the measuring unit of time is set to be longer as a size of the light detection region is larger and to be shorter as the moving speed of the light detection region is higher.

12. The method of claim 10, wherein the measuring unit of time is set so that a passage duration of one light-emitting particle passing through the light detection region overlaps with at least three measuring units of time.

13. The method of claim 10, further comprising (d) counting a number of signals indicating light from the light-emitting particles detected individually to count a number of the light-emitting particles detected during moving the position of the light detection region.

14. The method of claim 10, wherein, in the step (a), the position of the light detection region is moved at velocity quicker than a diffusion moving velocity of the light-emitting particle.

15. The method of claim 10, wherein, in the step (a), the position of the light detection region of the optical system is moved in the sample solution by changing an optical path of the optical system.

16. The method of claim 10, wherein, in the step (c), it is detected that one light-emitting particle has entered into the light detection region when a signal indicating light having a larger intensity than a predetermined threshold value is detected.

17. The method of claim 10, wherein, in the step (c), the time series light intensity data is smoothed, and a bell-shaped pulse form signal having an intensity beyond the predetermined threshold value in the smoothed time series light intensity data is detected as a signal indicating light from the single light-emitting particle.

18. The method of claim 10, further comprising: (e) determining a number density or concentration of the light-emitting particle in the sample solution based on a number of the detected light-emitting particles.

19. A computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising:
   moving a position of a light detection region of the optical system in the sample solution;
   detecting a light amount coming from the light detection region in every measuring unit of time during moving the position of the light detection region in the sample solution to generate time series light intensity data, the measuring unit of time being based on a size and a moving speed of the position of the light detection region during moving; and
   detecting individually a signal indicating light from each light-emitting particle using the time series light intensity data by detecting a time variation of light intensity having a profile expected in a light from one light-emitting particle moving relatively in the light detection region as a signal of one light-emitting particle,
   wherein the measuring unit of time is less than a half of an approximate passage duration of one light-emitting particle passing through the light detection region.

20. The computer readable storage device of claim 19, wherein the measuring unit of time is set to be longer as a size of the light detection region is larger and to be shorter as the moving speed of the light detection region is higher.

21. The computer readable storage device of claim 19, wherein the measuring unit of time is set so that a passage duration of one light-emitting particle passing through the light detection region overlaps with at least three measuring units of time.

22. The computer readable storage device of claim 19, said programmed instructions causing a computer to further perform a step of counting a number of signals indicating light from the light-emitting particles detected individually to count a number of the light-emitting particles detected during moving the position of the light detection region.

23. The computer readable storage device of claim 19, wherein, in the step of moving the position of the light detection region, the position of the light detection region is moved at velocity quicker than a diffusion moving velocity of the light-emitting particle.

24. The computer readable storage device of claim 19, wherein, in the step of moving the position of the light detection region, the position of the light detection region of the optical system is moved in the sample solution by changing an optical path of the optical system.

25. The computer readable storage device of claim 19, wherein, in the step of detecting the signal indicating light from each light-emitting particle individually, it is detected that one light-emitting particle has entered into the light detection region when a signal indicating light having a larger intensity than a predetermined threshold value is detected.

26. The computer readable storage device of claim 19, wherein, in the step of detecting the signal indicating light from each light-emitting particle individually, the time series light intensity data is smoothed, and a bell-shaped pulse form signal having an intensity beyond the predetermined threshold value in the smoothed time series light intensity data is detected as a signal indicating light from the single light-emitting particle.

27. The computer readable storage device of claim 19, said programmed instructions causing a computer to further perform a step of determining a number density or concentration of the light-emitting particle in the sample solution based on a number of the detected light-emitting particles.

* * * * *